United States Patent [19]

LeMaire et al.

[11] Patent Number: 5,344,915

[45] Date of Patent: Sep. 6, 1994

[54] PROTEINS AND THE PREPARATION THEREOF

[75] Inventors: Hans-Georg LeMaire, Dirmstein; Heinz Hillen, Hassloch, both of Fed. Rep. of Germany; Achim Moeller, Winchester, Mass.; Lothar Daum, Otterstadt, Fed. Rep. of Germany; Thomas Doerper, Bissersheim, Fed. Rep. of Germany; Thomas Subkowski, Mutterstadt, Fed. Rep. of Germany

[73] Assignee: BASF Aktiengesellschaft, Ludwigshafen, Fed. Rep. of Germany

[21] Appl. No.: 768,443

[22] PCT Filed: May 4, 1990

[86] PCT No.: PCT/EP90/00719

§ 371 Date: Sep. 26, 1991

§ 102(e) Date: Sep. 26, 1991

[87] PCT Pub. No.: WO90/13575

PCT Pub. Date: Nov. 15, 1990

[30] Foreign Application Priority Data

May 9, 1989 [DE] Fed. Rep. of Germany ....... 3915072
Jul. 5, 1989 [DE] Fed. Rep. of Germany ....... 3922089

[51] Int. Cl.$^5$ ............................................. C07K 15/06
[52] U.S. Cl. .................................. 530/350; 530/395; 530/413; 530/416
[58] Field of Search ................... 530/350, 395, 388.23, 530/413, 416; 435/69.5

[56] References Cited

U.S. PATENT DOCUMENTS

| 4,677,063 | 6/1987 | Mask et al. | 435/68 |
| 4,898,818 | 2/1990 | Nakai et al. | 435/69.1 |
| 4,948,875 | 8/1990 | Tanaka et al. | 530/350 |
| 4,990,455 | 2/1991 | Yamagishi et al. | 435/69.5 |

OTHER PUBLICATIONS

Seckinger, et al., "A Human Inhibitor of Tumor Necrosis . . . ", J. Exp. Med., vol. 167, pp. 1511–1516. (1988).
Peetre, Christina et al., "A Tumor Necrosis Factor . . . ", Eur. J. Haematol., vol. 41, pp. 414–419 (1988).
Schall et al., Cell, vol. 61, pp. 361–370, 1990.
Smith et al., Science, vol. 248, pp. 1019–1023, 1990.
Engelmann et al., "Two tumor necrosis factor-binding proteins . . . ", Jour. of Biol. Chemistry, vol. 265(3), 1990, pp. 1531–1536.
Engelmann et al., "Two TNF-Binding Proteins Purified from Human Urine", J. Biol. Chem., vol. 265, No. 3, Jan. 25, 1990, pp. 1531–1536.

Primary Examiner—Michael G. Wityshyn
Assistant Examiner—C. Sayala
Attorney, Agent, or Firm—Keil & Weinkauf

[57] ABSTRACT

Novel proteins which have a molecular weight of about 42,000 daltons and have at the N terminus the amino acid sequence Xaa Thr Pro Tyr Ala Pro Glu Pro Gly Set Thr Cys Arg Leu Arg Glu where X is hydrogen, a phenylalanine residue (Phe) or the amino acid sequences Ala Phe, Val Ala Phe, Gln Val Ala Phe, Ala Gln Val Ala Phe, Pro Ala Gln Val Ala Phe or Leu Pro Ala Gln Val Ala Phe, and which are suitable for the treatment of diseases, are described.

3 Claims, No Drawings

PROTEINS AND THE PREPARATION THEREOF

The present invention relates to novel proteins and the preparation thereof.

TNFα (tumor necrosis factor) is a known protein which has a broad spectrum of biological activities. It influences various malignant and non-malignant cell types, plays a part in septic shock and tissue injuries and in kidney rejections, transplantations, shock lung and cerebral malaria (Lymphokines 1987 Vol. 14; Pharmaceutical Res. 5 (1988), 129; Science 234 (1986), 470; Nature 330 (1987), 662; J. Exp. Med. 166 (1987), 1132; Science 237 (1987), 1210; J. Exp. Med. 166 (1987), 1280).

It is known that the action of TNFα can be neutralized by antibodies (EP 260 610). However, these antibodies are not human substances so that use on humans may lead to immunological reactions.

We have now found proteins which are of human origin and are able to neutralize the action of TNFα.

The present invention relates to proteins which have a molecular weight of about 42,000 daltons and have at the N terminus the amino acid sequences Xaa Thr Pro Tyr Ala Pro Glu Pro Gly Set Thr Cys Arg Leu Arg Glu where Xaa is hydrogen, a phenylalanine residue (Phe) or the amino acid sequences Ala Phe, Val Ala Phe, Gln Val Ala Phe, Ala Gln Val Ala Phe, Pro Ala Gln Val Ala Phe or Leu Pro Ala Gln Val Ala Phe, and the muteins thereof.

By muteins are meant proteins which are produced by suitable exchange, deletion or addition of amino acids or peptides in the protein chain without this leading to a large reduction in the action of the novel proteins. Muteins can also be obtained by altering the glycoside residue.

The novel proteins described herein have acidic properties, their leoelectric point being at pH 2 to 5. They bind very specifically to TNFα and are digestible by trypsin with difficulty or not at all.

The novel proteins can be isolated, for example, from the urine of patients with fever, ie. whose body temperature is about 38° C. or above. For this purpose, the urine is first concentrated, which can be effected, for example, by reverse osmosis or ultrafiltration. The retentate from this is then purified by ion exchange and affinity chromatography.

The proteins can also be obtained from ascites fluid from human patients with ovarian carcinomas.

The proteins can be purified by conventional methods such as affinity or ion exchange chromatography.

The proteins obtained in this way are inhomogeneous in the amino acid sequence at the N terminus. Up to 7 amino acids may be absent. Inhomogeneities of this type are not unusual with endogenous proteins and also occur, for example, in γ-interferon.

Treatment with an endoglycosidase alters the migration behavior of the protein in SDS polyacrylamide gel electrophoresis, and this is attributable to elimination of sugar residues.

The proteins described herein are present in urine and ascites fluid in concentrations of from 1 to 100 μg/l. Known genetic engineering methods (cf. Maniatis, T. et al.: Molecular Cloning: A Laboratory Manual, Cold Spring Harbor Press, N.Y., 1982) can be used to obtain the protein in larger Mounts for pharmaceutical purposes. It is necessary for this purpose initially to identify the genetic information for the novel protein and to isolate the corresponding nucleic acid. This entails the pure protein being reduced with dithiothreitol, then iodacetamide is added to derivatize the free SH groups, and subsequently the protein which has been treated in this way is cleaved with cyanogen bromide and then with trypsin into small peptides. The peptides are fractionated by reverse phase chromatography. N-terminal sequencing of one of these purified peptides reveals the sequence Val Phe Cys Thr Lys. The protein also contains the following three peptide sequences: Gly Val Tyr Thr Set, Ile Cys Thr Cys Arg Pro Gly Tyr and Pro Gly Thr Glu Thr Ser Asp Val Val Cys Lys Pro Cys Ala Pro Gly Thr Phe Ser Xab Thr Thr Ser Ser Asp Ile Cys Arg Pro, where Xab is an amino acid which has yet to be identified and is possibly glycosylated.

The available peptide sequences now permit, by synthesis of appropriate oligonucleotides, unambiguous identification of the gene from the human genome or from appropriate cDNA banks by sequence-specific filter hybridization.

The genetic information for the protein obtained in this way can then be expressed in various host cells such as eukaryotic cells, yeasts, Bacillus subtilis or E. coli by conventional methods, and the protein can thus be obtained. The protein produced in eukaryotic cells is glycosylated forth.

The muteins which are derived from the novel proteins by exchange, deletion or addition of amino acids or peptides are preferably prepared by genetic engineering methods.

The novel proteins display good TNFα—inhibiting actions and can therefore be used for the treatment of diseases in which the concentration of TNFα in body fluids is elevated, such as septic shock. They can also be used for the following disorders: allergies, auto-immune diseases, rheumatic disorders, shock lung, inflammatory bone disorders, disturbances of blood clotting, burns and complications following transplantations.

EXAMPLE 1

Determination of the TNFα-Inhibitory Action

The biological activity of TNFα was determined by lysis of the mouse cell line L929 (J. Biol. Chem. 260 (1985), 2345) and the human cell line MCF7. The concentration of TNFα chosen in experiments to determine the TNFα-inhibitory action was that which lysed at least 50% of the cells.

Supernatants containing TNFα-binding proteins were diluted in 1:2 steps in microtiter plates. 0.05 ml of human or murine TNFα (120 pg/ml) was added to each of these solutions (0.05 ml). Then 50,000 L929 cells in 0.1 ml of medium which contained 2 μg/ml actinomycin D were added. After incubation for 20–24 h at 37° C., the cells were fixed and stained with crystal violet. In the absence of TNFα-binding protein, TNFα and LT (11 lymphotoxin) lysed the cells. The latter were floated off during the staining. The protective effect of supernatants containing TNFα-binding proteins was evident from the staining of intact cells, which remained.

There was found to be an inhibition of the cytotoxic action both of human TNFα and, somewhat less strongly, of human LT, but not of murine TNFα.

EXAMPLE 2

Isolation of Protein From Urine 40 l of urine collected from patients with fever (≧38° C.) was filtered through a Hemoflow ® F60 cartridge (from Fresenius) until the voluble of the retentate flow had been concentrated to 2.5 l.

The retentate was then washed by 4 additions of 2.5 l of 20 mM sodium phosphate buffer pH 4.0 and continuation of the filtration each time until the volume had returned to the initial 2.5 l.

The protein-rich, broken retentate obtained in this way was chromatographed on S-Sepharose ® from Pharmacia (column: i.d.=5 cm, 1=17 cm). The column was equilibrated with 10 column volumes (CV) of 20 mM sodium phosphate buffer, pH 5.5 (=buffer I), and the retentate was then loaded on. The column was then washed with 3 CV of buffer I, and the required product was obtained by elution with 3 CV of a 20 mM sodium phosphate buffer, pH 6.5 (buffer II).

For further purification of this fraction, it was loaded onto a TNF affinity column (Example 4) (i.d.=1.5 cm, 1=10 cm) which had been equilibrated with 10 CV of buffer III (20 mM sodium phosphate, 140 mM NaCl, pH 7.2). After loading, the column was washed with 3 CV of buffer III, and the TNF-binding protein fraction was eluted from the column with 40 ml of buffer IV, composed of 0.58% acetic acid and 140 mM NaCl.

The pure protein was isolated by fractionating the eluate from the TNF affinity colan on a Mono Q HR 5/5 column from Pharmacia after the eluate had been adjusted to pH 12.0 with 0.1N NaOH.

The column was equilibrated with 11 CV of 20 mM sodin phosphate buffer pH 12.0 (buffer V). 10 ml of the pH-adjusted TNF affinity column eluate were loaded on, and the column was washed with 4.4 CV of buffer V. It was then eluted with 20 mM sodium phosphate pH 7.5.

For further removal of impurities, the Mono Q column was washed with 7 CV of 20 mM acetic acid buffer which had been adjusted to pH 2.0 with 0.1N HCl (buffer VI).

The column was then further eluted with 5–6 CV of 20 mM acetic acid, 20 mM $NH_4Cl$ buffer, pH 2.0 (adjusted with 0.1N HCl, buffer VII). A band which was UV-active at 280 nm and contained impurities eluted after 1–2 CV, and the novel protein eluted after a further 1–2 CV. A further amount of pure protein can be obtained by subsequent elution with 1–2 CV of a buffer VII adjusted to 100 mM NaCl.

The protein obtained in this way had a purity >90% by gel electrophoresis. About 1 to 10 μg of protein can be obtained from 1 l of urine.

EXAMPLE 3

Isolation of Protein From Human Ascites Fluid 2.5 l of slightly cloudy, thin ascites fluid which was obtained from a patient with ovarian carcinoma by puncture was centrifuged at 3000×g for 30 min. The supernatant was adjusted to pH 7.2 with 10% strength phosphoric acid and loaded onto a glutaraldehyde-crosslinked TNF-Sepharose ® (cf. Example 4) column (i.d.= 1.5 cm, 1=3 cm). The column was equilibrated with 50 ml of buffer III and, after loading, washed with 150 ml of buffer III. The TNF-binding proteins were eluted with 30 ml of buffer IV.

For further purification, the eluate was adjusted to pH 3.0 with 10% strength HCl and loaded onto a column (Mono S HR 5/5 from Pharmacia) equilibrated with 20 mM acetic acid (pH 3.0). The column was then washed with 10 ml of 20 mM acetic acid (pH 3.0) and the TNF-binding proteins were subsequently eluted with 4 ml of a buffer composed of 6 parts of 20 mM acetic acid (pH 3.0) and 4 parts of 50mM sodium phosphate buffer (pH 9.0). The pH of the eluate was monitored and adjusted to pH 6.5 if necessary.

The eluate was loaded onto a Mono Q HR 5/5 column equilibrated with sodium phosphate buffer pH 6.0 (buffer VIII). After washing with 6 ml of buffer VIII and 6 ml of 20 mM acetic acid, 5 mM NaCl, pH 2.2, the protein was eluted with 6 ml of 20 mM acetic acid, 150 mM NaCl, pH 2.0 (buffer IX).

Characterization of the final eluate revealed that, apart from the inhomogeneity of the N-terminal sequence, the protein was the same as that obtained in Example 2.

EXAMPLE 4

Preparation of the TNF Affinity Column a) Coupling of TNF to BrCN-Sepharose 7.5 g of BrCN-Sepharose ® (from Pharmacia) were suspended in 30 ml of water. After swelling for 30 min, the BrCN-Sepharose ® gel suspension was washed first with 500 ml of 1 mM HCl solution and then with 0.1M $NaHCO_3$, 0.5M NaCl, pH 8.3.

136 mg of TNF dissolved in 41 ml of buffer (0.1M $NaHCO_3$, 0.5M NaCl, pH 8.3) were added to this gel suspension. The reaction mixture was shaken at room temperature for 2 h, and the TNF-Sepharose ® was removed by centrifugation at 3000 rpm. The gel material was washed with 40 ml of buffer.

The coupling yield calculated from determination of the protein in the supernatants was >90%.

To block the remaining active groups on the BrCN-Sepharose ®, the gel suspension was mixed with 40 ml of buffer (0.1M $NaHCO_3$, 0.5M NaCl, 1M ethanolamine, pH 8.3) and shaken at room temperature for 1 h, and the ethanolmine was then washed out with 3×40 ml of buffer (0.1M $NaHCO_3$, 0.5M NaCl, pH 8.3).

b) Crosslinking of the TNF-Sepharose ® with glutaraldehyde 20 ml of TNF-Sepharose ® gel suspension prepared as in a) were washed twice with 25 ml of buffer (20 mM sodium phosphate, 140 mM NaCl, pH 8.0). The suspension was taken up in 40 ml of the same buffer, and 1.6 ml of 25% strength glutaraldehyde solution were added. The suspension was shaken at room temperature for 1 h and then centrifuged, and 25 ml of buffer (20 mM sodium phosphate, 140 mM NaCl, 1M ethanolamine, pH 8.0) were added. The TNF-Sepharose ® suspension was shaken for a further 1 h and then packed into a chromatography column (i.d.=1.5 cm, 1=10 cm).

The column was washed with 100 ml of buffer (20 mM sodium phosphate, 140 mM NaCl, pH 7.2) and 50 ml of 0.58% acetic acid+140 mM NaCl and was then ready for affinity chromatography.

EXAMPLE 5

Characterization of the Protein a) Molecular Weight and Purity

To determine the molecular weight and the purity, 2 μg of the protein obtained as in Example 2 or 3 were subjected to 15% SDS polyacrylamide gel electrophoresis under reducing and non-reducing conditions (Nature 227 (1970), 680). In both methods, the novel protein was revealed after staining with Coomassie blue as a homogeneous band with a molecular weight of about 42,000 daltons by comparison with a series of known calibration proteins.

No other bands were detectable. The purity of the protein can thus be stated to be ≧90%.

The protein is evident as a distinct blue-violet band.

b) N-terminal Sequencing

10 μg (≈250 pmol) of the protein obtained in Example 2 underwent N-terminal sequencing in a gas-phase sequencer several times.

The occurrence of related additional sequences in the N-terminal sequence analysis indicates the inhomogeneity of the N-terminal amino acid sequence. The main sequences found were as follows: Sequence 1a Phe Thr Pro Tyr Ala Pro Glu Pro Gly Set Thr Cys Arg Leu Arg Glu Also found in the gas-phase sequencing were a Sequence 2a
Leu Pro Ala Gln Val Ala Phe Thr Pro Tyr Ala Pro Glu Pro Gly Ser Thr Cys Arg Leu Arg Glu
with an N-terminal extension of 6 amino acids and a
Sequence 3a
Thr Pro Tyr Ala Pro Glu Pro Gly Ser Thr Cys Arg Leu Arg Glu
shortened by 1 N-terminal amino acid.
The main sequences found in a similar manner in the protein of Example 3 were as follows:
Sequence 1b
Leu Pro Ala Gln Val Ala Phe Thr Pro Tyr Ala Pro Glu Pro Gly Ser Thr Cys Arg Leu Arg Glu (about 10%)
Sequence 2b
Pro Ala Gln Val Ala Phe Thr Pro Tyr Ala Pro Glu Pro Gly Ser Thr Cys Arg Leu Arg Glu (about 45%)
Sequence 3b
Ala Gln Val Ala Phe Thr Pro Tyr Ala Pro Glu Pro Gly Ser Thr Cys Arg Leu Arg Glu (about 45%)

d) Trypsin Treatment

20 μg of the novel proteins were treated at pH 8.5 as follows:

1. Addition of 0.5 μg of trypsin dissolved in 0.1M NaHCO₃ buffer pH 8.5; incubation at 37° C. for 16 h 2. Addition of 0.5 μg of trypsin dissolved in 0.1% SDS/0.1M NaHCO₃ buffer pH 8.5; solution adjusted to 0.1% SDS; incubation at 37° C. for 16 h.

The proteins treated in this way were compared with the initial protein in a 15% SDS polyacryleunide gel electrophoresis. No protein degradation was detectable.

EXAMPLE 6

Deglycosylation 0.1 ml of the Mono Q eluate obtained in Example 2 (=0.1 mg/ml protein) was adjusted to pH 7.2 with 1M NaOH. 10 units of glycopeptidase F (from Boehringer Mannheim) were then added. After incubation at 37° C. for 6 h, a further 10 units of enzyme were added. After reaction for a further 16 h, 50 μl of the mixture were freeze-dried and compared with untreated protein in a 15% SDS gel. The enzyme-treated protein showed a molecular weight about 3 kD less than that of the untreated sample. A further 25 μl of the mixture were tested for TNFα-inhibiting action as described in Example 1. The TNFα-inhibiting action was fully retained even after elimination of the sugar portion.

EXAMPLE 7

Antibody Production

The proteins isolated in Examples 2 and 3 were injected into rabbits for the production of polyclonal antibodies. The reactivity and specificity of the antibodies were examined in an ELISA. This entailed ELISA plates (from Costar) being coated with a solution of 1 μg of inhibitor or control protein per ml of 0.05M sodium carbonate buffer, pH 9.6, treated with 1% BSA/PBS to saturate non-specific binding and incubated with various serum dilutions. The bound antibodies were detected using biotinylated anti-rabbit IgG and streptavidin-peroxidase, plus TMB substrate. 3 washes with 0.05% ®Tween 20/PBS were carried out between each incubation. Addition of 2M H₂SO₄ was followed by determination of the optical density at 450 nm.

EXAMPLE 8

Detection of Protein in Body Fluids

TNFα-binding proteins were detected in various body fluids using a sandwich ELISA. ELISA plates (from Costar) were coated with TNF (5 μg/ml of 0.05M sodium carbonate buffer, pH 9.6). Saturation with 1% BSA/PBS was followed by incubation with the test samples, eg. synovial fluids from rheumatic patients. The anti-inhibitor antibodies described in Example 7 and biotinylated antirabbit IgG/streptavidin-peroxidase/TMB substrate were used for detection. 3 washes with 0.05% ®Tween 20/PBS were carried out between each incubation. The extinction at 450 nm was determined after addition of 2M H₂SO₄.

We claim:

1. A purified and isolated TNFα-binding protein which has a molecular weight of about 42,000 daltons and has at the N terminus the amino acid sequence Xaa Thr Pro Tyr Ala Pro Glu Pro Gly Set Thr Cys Arg Leu Arg Glu where Xaa is hydrogen, a phenylalanine residue (Phe) or the amino acid sequences Ala Phe, Val Ala Phe, Gln Val Ala Phe, Ala Gln Val Ala Phe, Pro Ala Gln Val Ala Phe or Leu Pro Ala Gln Val Ala Phe.

2. A protein as claimed in claim 1 in deglycosylated form.

3. A process for the preparation of a protein which has a molecular weight of about 42,000 daltons and has at the N terminus the amino acid sequence Xaa Thr Pro Tyr Ala Pro Glu Pro Gly Set Thr Cys Arg Leu Arg Glu where Xaa is hydrogen, a phenylalanine residue (Phe) or the amino acid sequences Ala Phe, Val Ala Phe, Gln Val Ala Phe, Ala Gln Val Ala Phe, Pro Ala Gln Val Ala Phe or Leu Pro Ala Gln Val Ala Phe, which comprises concentration of the urine of patients with fever and subsequent purification of the retentate obtained in this way by ion exchange and affinity chromatography.

* * * * *

UNITED STATES PATENT AND TRADEMARK OFFICE
CERTIFICATE OF CORRECTION

PATENT NO.: 5,344,915

DATED: September 6, 1994

INVENTOR(S): LEMAIRE et al.

It is certified that error appears in the above-identified patent and that said Letters Patent is hereby corrected as shown below:

Cover page, item [57], line 4 of the Abstract, "Set" should read --Ser--.

Column 6, claim 1, line 41, "Set" should read --Ser--.

Column 6, claim 3, line 52, "Set" should read --Ser--.

Signed and Sealed this

Twenty-ninth Day of November, 1994

Attest:

BRUCE LEHMAN

Attesting Officer

Commissioner of Patents and Trademarks